(12) United States Patent
Moore et al.

(10) Patent No.: US 6,723,569 B1
(45) Date of Patent: Apr. 20, 2004

(54) LIQUID TRANSFER SYSTEM

(75) Inventors: David Frank Moore, Cambridge (GB); William Ireland Milne, Cambridge (GB); Martin Clement Davies, Comberton (GB); Stuart Antony Elmes, Comberton (GB)

(73) Assignee: Genomic Solutions Acquisitions Limited, Cambridgeshire (GB)

( * ) Notice: Subject to any disclaimer, the term of this patent is extended or adjusted under 35 U.S.C. 154(b) by 0 days.

(21) Appl. No.: 09/831,132

(22) PCT Filed: Nov. 1, 1999

(86) PCT No.: PCT/GB99/03588
§ 371 (c)(1),
(2), (4) Date: Aug. 13, 2001

(87) PCT Pub. No.: WO00/25923
PCT Pub. Date: May 11, 2000

(30) Foreign Application Priority Data

Nov. 4, 1998  (GB) .............................................. 9824202

(51) Int. Cl.$^7$ .................................................. G01N 1/10
(52) U.S. Cl. ..................... 436/180; 73/864.02; 101/494; 422/100
(58) Field of Search ......................... 422/100; 436/180; 101/494; 73/864.02

(56) References Cited

U.S. PATENT DOCUMENTS

| | | | | |
|---|---|---|---|---|
| 4,971,763 A | * | 11/1990 | Columbus | 422/100 |
| 5,334,353 A | | 8/1994 | Blattner | 422/100 |
| 5,601,980 A | * | 2/1997 | Gordon et al. | 435/6 |
| 5,756,050 A | | 5/1998 | Ershow et al. | 422/100 |
| 5,763,278 A | | 6/1998 | Sickinger et al. | 436/180 |
| 5,770,151 A | * | 6/1998 | Roach et al. | 422/63 |
| 5,770,860 A | | 6/1998 | Franzen | 250/288 |
| 6,051,190 A | * | 4/2000 | Birch et al. | 422/100 |
| 6,101,946 A | * | 8/2000 | Martinsky | 101/494 |
| 6,350,618 B1 | * | 2/2002 | Borrelli et al. | 436/174 |

FOREIGN PATENT DOCUMENTS

| | | |
|---|---|---|
| DE | 19847421 A1 | 4/2000 |
| EP | 0364203 A1 | 4/1990 |
| EP | 0641599 A1 | 3/1995 |
| EP | 0768519 A2 | 4/1997 |
| WO | WO 98/15355 | 4/1998 |
| WO | WO 98/57747 | 12/1998 |

OTHER PUBLICATIONS

Webster's Ninth New Collegiate Dictionary, Merriam–Webster Inc., Springfield, Mass. (1987), pp. 892–893.*

* cited by examiner

*Primary Examiner*—Jan Ludlow
(74) *Attorney, Agent, or Firm*—Wolf, Greenfield & Sacks, P.C.

(57) ABSTRACT

A dropping tool for transferring drops of a liquid onto a substrate wherein a surface of the dropping tool for contact with the liquid has a first region which exhibits an affinity to the liquid to be transferred directly surrounded by a second region which exhibits a lower affinity to the liquid to be transferred than the first region; the topography of the first and second regions and the relative affinities of the first and second regions for the liquid to be transferred being selected such that when the dropping tool is dipped into and then removed from a source of the liquid to be transferred, the liquid adheres to the first region without substantially any adherence of the liquid to the second region. A dropping tool for transferring drops of liquid onto a substrate, the dropping tool comprising a tip, at least one surface tapered towards the tip, and a capillary channel which leads from a position of the tapered surface remote from the tip to a reservoir located within the dropping tool. A method for transferring drops of liquid carried on a dropping tool onto a substrate to form an ordered array of drops thereon wherein the drop of liquid is transferred without contacting the dropping tool with the substrate either directly or indirectly via the drop of liquid.

17 Claims, 3 Drawing Sheets

LIQUID TRANSFER SYSTEM

RELATED APPLICATIONS

This application claims the benefit under 35 U.S.C. §120 or 35 U.S.C. §365(c) of PCT International application PCT/GB99/03588, designating the United States of America, and filed Nov. 1, 1999. PCT application PCT/GB99/03588, of which this application is a national stage filing under 35 U.S.C. §371, was published under PCT Article 21(2) in English.

FIELD OF THE INVENTION

The present invention relates to tools and methods for dispensing an ordered array of liquid drops onto a solid substrate, particularly for multiple testing in the biotecitnological field.

BACKGROUND OF THE INVENTION

In the biotechnological field, it is often necessary to dispense liquid drops in an ordered array onto a solid substrate for performing multiple tests. There has been a strong desire to reduce the size of each individual liquid drop transferred on to the substrate so as to be able to increase the density of dots per unit area of substrate and at the same time minimize the volumes of expensive reagents required for the tests.

SUMMARY OF THE INVENTION

It is an aim of the present invention to provide a dropping tool for dispensing drops of liquid on to a solid substrate which is of relatively simple construction and with which it is possible to dispense drops of relatively small size with excellent reproducibility.

It is another aim of the present invention to provide an alternative and improved method for transferring a drop of liquid carried on a dropping tool on to a target substrate.

According to a first aspect of the present invention, there is provided a use of a dropping tool in a method of transferring drops of liquid on to a substrate, wherein a surface of the dropping tool for contact with the liquid has a first region which exhibits an affinity to the liquid to be transferred directly surrounded by a second region which exhibits a lower affinity to the liquid to be transferred than the first region: the topography of the first and second regions and the relative affinities of the first and second regions for the liquid to be transferred being selected such that when the dropping tool is dipped into and then removed from a source of the liquid to be transferred, the liquid adheres to the first region without substantially any adherence of the liquid to the second region.

According to a second aspect of the present invention, there is provided a dropping tool for transferring drops of a liquid onto a substrate wherein a surface of the dropping tool for contact with the liquid has a first region which exhibits an affinity to the liquid to be transferred directly surrounded by a second region which exhibits a lower affinity to the liquid to be transferred than the first region; the topography of the first and second regions and the relative affinities of the first and second regions for the liquid to be transferred being selected such that when the dropping tool is dipped into and then removed from a source of the liquid to be transferred, the liquid adheres to the first region without substantially any adherence of the liquid to the second region.

According to a third aspect of the present invention, there is provided a method for transferring drops of liquid carried on a dropping tool on to a substrate to form an ordered array of drops thereon wherein the drop of liquid is transferred without contacting the dropping tool with the substrate either directly or indirectly via the drop of liquid.

According to a fourth aspect of the present invention, there is provided a dropping tool for transferring drops of liquid on to a substrate, the dropping tool comprising a tip, at least one surface tapered towards the tip, and a capillary channel which leads from a position of the tapered surface remote from the tip to a reservoir located within the dropping tool.

BRIEF DESCRIPTION OF THE DRAWINGS

Embodiments of the present invention will now be described hereunder, by way of example only, with reference to the accompanying drawings in which:

FIG. 1 shows a cross-sectional view of the lower section of a dropping tool according to a first embodiment of the present invention for transferring drops of an aqueous liquid onto a solid substrate. In this embodiment the dropping tool is a steel pin substrate 12 having its whole surface other than a region at its tip 14 coated with a layer 16 of a relatively hydrophobic material such as teflon or tetrahedral amorphous carbon (t.a.C). The exposed area at the tip 14 is preferably generally circular in shape when viewed down the axis of the pin from the tip of the pin, and its size is determined in accordance with the desired drop size but will generally be of the order of a fraction of a mm, preferably about 0.1 mm or less. In this first embodiment, the boundary between the exposed steel tip of the pin and the relatively hydrophilic coating is topologically continuous. This dropping tool can be fabricated by removing a small thickness of surface steel from the portion of the surface of a conventional steel dropping pin surrounding the tip of the pin followed by subsequent application of a layer of the relatively hydrophobic material onto the region of the pin from which the layer of steel has been removed. The removal of the layer of steel can be carried out by a mechanical process or by physical or chemical etching. The application of the layer of relatively hydrophobic material can, for example, be carried out by filtered vacuum arc (fcva), plasma enhanced chemical vapour deposition (pecvd), evaporation or by dipping the relevant portion of the pin in a liquid of the material. Plasma-enhanced chemical vapour deposition is the preferred method of application.

The selection of the material used for the relatively hydrophobic region will depend on the desired drop size. For example, particularly small tip sizes (for producing particularly small drops) will require the selection of a material which is much less hydrophilic than the exposed steel tip of the pin if the drop of liquid is to be contained within the bounds of the exposed hydrophilic tip of the dropping pin.

Figure 2:
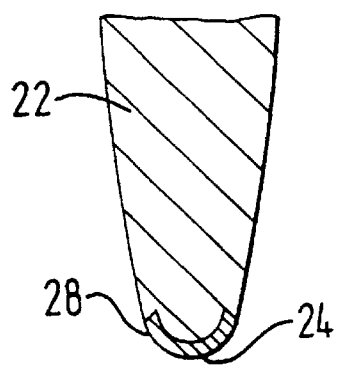

FIG. 2 shows a cross-sectional view of the lower section of a dropping tool according to a second embodiment of the present invention for dispensing drops of an aqueous liquid on to a solid substrate. In this second embodiment, a pin substrate 22 made of a relatively hydrophobic material such as teflon is provided at its tip 24 with a thin circular layer 28 of a hydrophilic material such as platinum. As in the first embodiment, the boundary between the layer of hydrophilic material and the non-coated surface of the hydrophobic pin substrate is topologically continuous.

Figure 3:
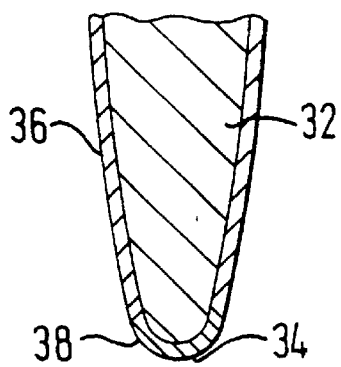

FIG. 3 shows a cross-sectional view of the lower section of a dropping tool according to a third embodiment of the present invention for dispensing drops of an aqueous liquid onto a solid substrate. A steel pin substrate 32 is coated at its tip 34 with a thin layer 38 of a hydrophilic material such as hydrogenated amorphous carbon, and the region of the pin surrounding the coated tip is coated with a thin layer 36 of a hydrophobic material such as teflon. As in the first two embodiments, the boundary between the hydrophilic tip and hydrophobic region surrounding the tip is topologically continuous. The layer 38 of hydrophilic material is preferably generally circular in shape when viewed down the axis of the pin from the tip of the pin.

Figure 1:
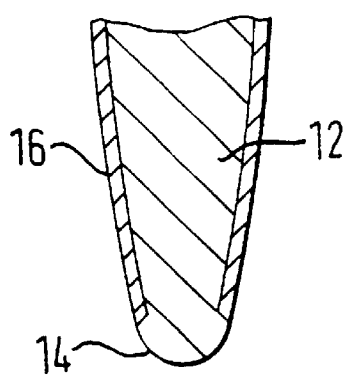
FIGS. 1 to 15 are schematic cross-sectional views of the lower sections of dropping tools according to fifteen different embodiments of the present invention respectively.
Figure 4:
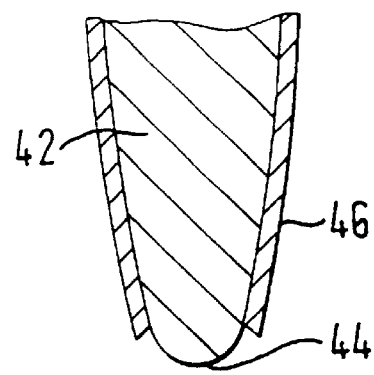

FIG. 4 shows a cross-sectional view of the lower section of a dropping tool according to a fourth embodiment of the present invention. This embodiment is similar to the first embodiment except that the layer 46 of relatively hydrophobic material is coated on a steel pin substrate 42 having a continuous surface such that there is a topological step at the boundary between the relatively hydrophobic layer and the exposed tip 44 of the pin in the resulting dropping tool. In other words, the relatively hydrophobic layer protrudes further than the underlying material. This makes it further energetically favourable for the liquid drop to terminate at the interface, and thus improves the uniformity of drop size.

Figure 5:
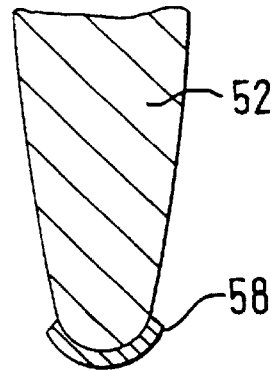

FIG. 5 shows a cross-sectional view of the lower section of a dropping tool according to a fifth embodiment of the present invention. This embodiment is similar to the second embodiment except that the layer of hydrophilic material 58 (such as platinum metal) is formed on the tip of a pin substrate 52 which is made of a relatively hydrophobic material (such as teflon) and has a continuous surface- with the result that there is a topological step at the boundary between the surface of the relatively hydrophobic pin substrate 52 and the hydrophilic layer 58. This has the same kind of advantages as those described for the fourth embodiment.

Figure 6:
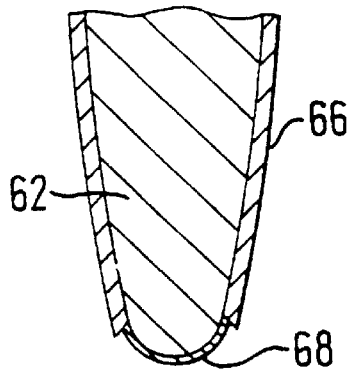

FIG. 6 shows a cross-sectional view of the lower section of a dropping tool according to a sixth embodiment of the present invention. This embodiment is similar to the third embodiment except that the thickness of the layer 66 of relatively hydrophobic material is greater than the thickness of the layer 68 of the hydrophilic material resulting in a topological step at the boundary between the two layers. This construction also has the same kind of advantages as those described above for the fourth embodiment.

Figure 7:
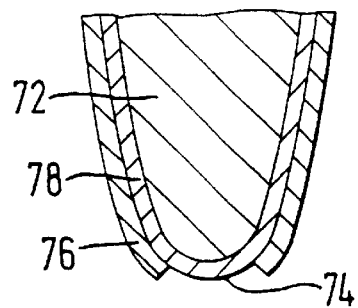

FIG. 7 shows a cross-sectional view of the lower section of a dropping tool according to a seventh embodiment of the present invention. A pin-shaped substrate 72 has a layer 78 of a hydrophilic material such as hydrogenated amorphous carbon over its entire surface. A layer 76 of a relatively hydrophobic material such as teflon is formed over the entire surface of the layer of hydrophilic material except for a region 74 at the tip of the pin to leave the layer of relatively hydrophilic material exposed. The exposed region is preferably generally circular in shape when viewed down the axis of the pin from the tip of the pin.

Figure 8:
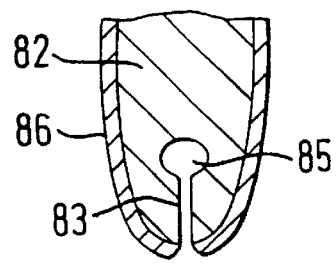

FIG. 8 shows a cross-sectional view of the lower section of a dropping tool according to an eighth embodiment of the present invention. A steel pin substrate 82 has a capillary channel 8, running vertically from its tip to a reservoir 85 located inside the steel pin substrate 82. The surface of the pin substrate 82 surrounding the entrance to the capillary channel 83 is coated with a thin layer 86 of a relatively hydrophobic material such as teflon. This construction allows for the transfer of a plurality of drops (for example, ten drops) of uniform size without having to revisit the source of liquid after the transfer of each drop.

DETAILED DESCRIPTION

The above-described dropping pins are used in the following manner. The dropping pin is dipped into and then removed from a source of the liquid to be transferred. A drop of liquid remains adhered to the hydrophilic tip of the pin but not to the relatively hydrophobic region surrounding the tip of the pin, ensuring that a liquid drop of uniform size is loaded onto the dropping pin each time the pin is dipped into and then removed from the liquid source. The liquid drop can then be transferred to a solid substrate in a number of ways. For example, it can be deposited by the conventional method of bringing the tip of the dropping pin into close proximity with the surface of the solid substrate such that the drop of liquid makes simultaneous contact with the surface of the solid substrate. Provided that the surface of the solid substrate is not less hydrophilic than the tip of the dropping pin, the drop of liquid transfers to the solid substrate when the dropping tool is then withdrawn from the surface of the solid substrate.

Alternatively, the liquid drop can also be transferred by the new transfer methods of the present invention. In one such method, the tip of the dropping pin is accelerated down towards the surface of the solid substrate and then stopped at a high rate of deacceleration at a position above the surface of the solid substrate where the drop of liquid does not make simultaneous contact with the surface of the solid substrate. The momentum of the liquid drop causes it to become projected from the tip of the pin on to the surface of the solid substrate.

In an alternative transfer method, the tip of the dropping pin is brought into a position above the surface of the solid substrate where the drop of liquid does not make simultaneous contact with the surface of the solid substrate. A pressure wave is then induced in the body of the pin such that it is focussed at the point of the pin where the liquid drop is being carried (i.e. the tip). The pressure wave causes the drop of liquid to become projected from the tip of the pin on to the substrate. The pressure wave can be created by physically tapping the end of the pin opposite to its tip or by other non-mechanical means such as piezoelectric or electromagnetic effects.

The two methods of the present invention described above have the advantage that it is not necessary to ensure that the tip of the pin is less hydrophilic than the surface of the solid substrate onto which the liquid drop is transferred, and the materials used to make the pin can therefore be selected regardless of the nature of the substrate onto which the drop of liquid is to be transferred.

Figure 9:
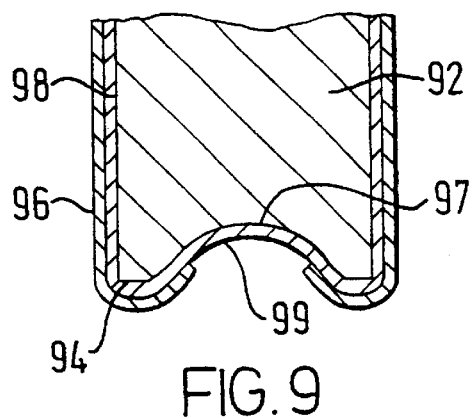

FIG. 9 shows a cross-sectional view of a dropping tool according to a ninth embodiment of the present invention. In this embodiment, a pin substrate having a squared-off tip is provided with a recess 97 at its tip. A layer 98 of a hydrophilic material is formed over the entire surface of the pin substrate 92, and a second layer 96 of a relatively hydrophobic material is formed over the entire surface of the layer 98 of hydrophilic material except for a circular (when viewed down the axis of the pin) region 99 in the recess 97 at the tip of the pin. The recess is preferably made deep enough that a drop of liquid carried on the hydrophilic region of the recess of the pin does not make contact with the surface of a solid substrate when the squared-off portion 94 of the tip of the pin is brought into contact therewith. The drop of liquid can then be transferred from the pin on to the solid substrate by impacting the squared-off portion 94 of the tip of the pin with the surface of the solid substrate whereby the drop of liquid carried in the recess is projected from the pin onto the surface of the solid substrate by its own momentun. The drop of liquid could of course also be transferred by the two non-contact methods described above.

Figure 10:
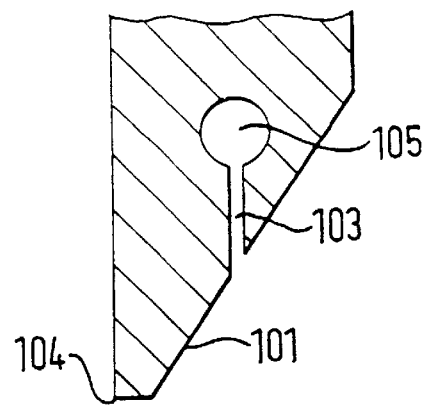

FIG. 10 shows a cross-sectional view of the lower section of a dropping tool according to a tenth embodiment of the present invention. The steel dropping tool is wedge shaped with a squared-off tip 104 and a tapered face 101 tapered towards the squared-off tip 104. A capillary channel 103 extends from the tapered face 101 to a reservoir 105 located within the dropping tool. The capillary channel 103 is preferably formed so as to extend in a direction approxiamately perpendicular to the squared-off tip 104. The capillary channel 103 and reservoir 105 can be formed for example by electron discharge machining (EDM), laser ablation or by focussed ion beam etching. In use, the dropping tool is dipped into a source of the liquid to be transferred to fill the reservoir 105 and capillary channel 103. The squared-off tip 104 of the dropping tool is then impacted against the surface of the target solid substrate at an appropriate velocity such that a single drop of liquid is projected from the entrance of the capillary channel on to the surface of the solid substrate by a momentum effect.

Figure 11:
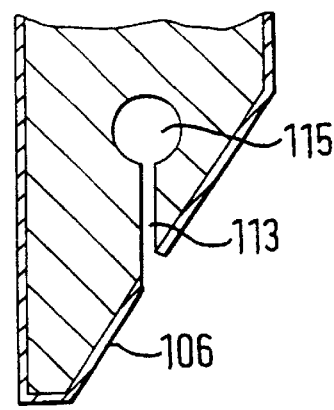

FIG. 11 shows a cross-sectional view of a dropping tool according to an eleventh embodiment of the present invention. This embodiment is identical to the tenth embodiment except that a layer 106 of relatively hydrophobic material such as teflon is formed on the entire surface of the dropping tool surrounding the entrance to the capillary channel 113. This deters liquid at the entrance to the capillary channel 113 from spreading onto the surrounding surface of the dropping tool whereby the uniformity of drop size can be further improved.

Figure 12:
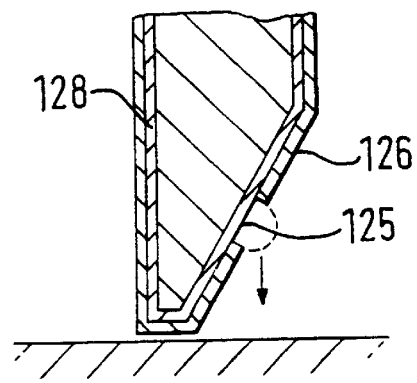

FIG. 12 shows a cross-sectional view of a dropping tool according to a twelfth embodiment of the present invention. This embodiment is similar to the tenth embodiment except that it does not have a capillary channel leading from the tapered surface to a reservoir. Instead, a layer 128 of hydrophilic material such as hydrogenated amorphous carbon is formed over the entire surface of the dropping tool, and a second layer 126 of relatively hydrophobic material, such as teflon, is formed over the entire surface of the layer of hydrophilic material except for a circular region 125 thereof on the tapered surface. When the dropping tool is dipped into a source of the liquid to be transferred, a drop of liquid adheres only to the exposed circular region 125 of the hydrophilic layer 128. The drop of liquid can then be transferred from the dropping tool to the target solid substrate by the impact method described above.

In FIGS. 10, 11 and 12, the entrance to the capillary channel (in the cases of FIGS. 10 and 11) or the region of hydrophilic material (in the case of FIG. 12) is well separated from the tip of the dropping tool. However, it is also possible to have the same at a position much closer to the tip of the pin such that when the tip of the pin is brought into contact with a solid substrate, liquid carried at the entrance to the capillary channel or on the region of hydrophilic material makes simultaneous contact with the solid substrate and the dropping tool, whereby a drop of the liquid is transferred from the dropping tool to the solid substrate when the dropping pin is subsequently withdrawn from the solid substrate.

In each of the dropping tools described above, the size of the hydrophilic region of the surface of the tool or the size of the entrance to the capillary channel in the case of the eighth, tenth and eleventh embodiments is determined in accordance with the desired drop size. Desired drop sizes are typically of the order of a fraction of a mm, preferably about 0.1 mm or less.

Figure 13:
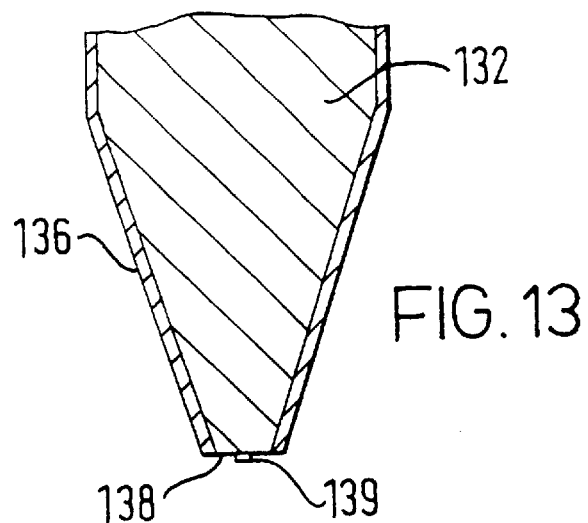

In the case of those embodiments which do not have a capillary channel, the dropping performance can be further improved by forming a third region of a relatively hydrophobic material at the center of the hydrophilic region. A schematic cross-sectional view of such an embodiment is shown in FIG. 13. A steel pin substrate 132 has a squared-off circular tip 138 having a diameter of about 0.1 mm. The tapered surface of the pin substrate 132 leading towards the squared-off tip is coated with a thin layer 136 of a hydrophobic material. A small circular area at the center of the squared-off tip is coated with a thin layer 139 of a material which is less hydrophilic than the exposed surface of the steel pin but is preferably less hydrophobic than the layer 136 of relatively hydrophobic material surrounding the squared-off tip 138 of the pin. This third region functions to further ensure that the liquid is transferred from the dropping pin to the target substrate as a droplet.

Figure 14:
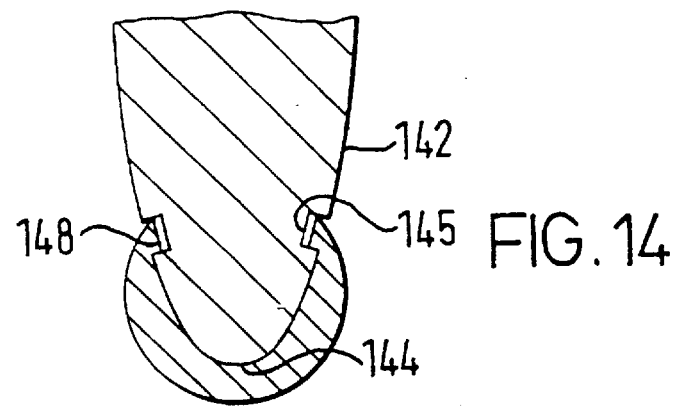

FIG. 14 shows a cross-sectional view of the lower section of a dropping tool according to a fourteenth embodiment of the present invention with a drop of an aqueous liquid carried on the pin. In this embodiment, an annular groove 145 is cut into a pin substrate 142 made of a relatively hydrophobic material (such as teflon) at a position distanced axially from the tip 144 of the pin. A layer of hydrophilic material such as hydrogenated amorphous carbon is applied to the groove to form a hydrophilic collar 148. The width of the collar 148 and the distance of the collar 148 from the tip of the pin is determined in accordance with the desired drop size. Desired drop sizes are typically of the order of a fraction of a mm, preferably 0.1 mm or less.

When the dropping pin is dipped into and subsequently removed from a source of the aqueous liquid to be transferred, a drop of liquid remains adhered to the section of the surface of the dropping pin comprising the hydrophilic collar and the region at the tip of the pin encompassed by the hydrophilic collar.

Figure 15:
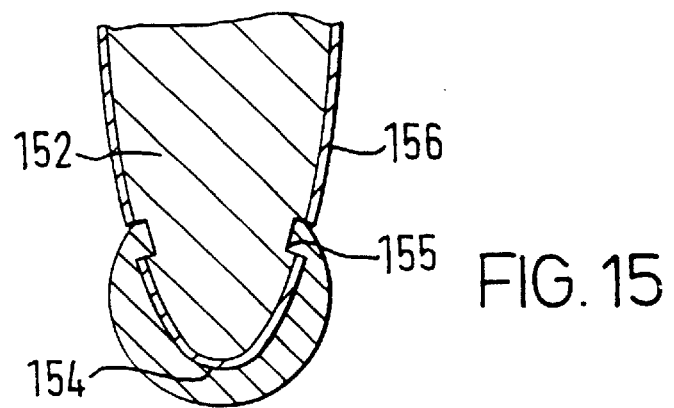

FIG. 15 shows a schematic cross-sectional view of a dropping pin according to a fifteenth embodiment of the present invention with a drop of aqueous liquid carried thereupon. This embodiment is similar in principle to the embodiment shown in FIG. 14. A steel pin subtrate 152 is first coated with a layer 156 of a relatively hydrophobic material such as teflon or tetrahedral amorphous carbon over its entire surface, and then an annular groove is then cut into the pin at a position distanced axially from the tip 154 of the pin to expose a collar of steel 155. As in the embodiment shown in FIG. 14, the width of the collar and the distance of the collar from the tip of the pin is determined in accordance with the desired drop size.

The examples of dropping tools described in detail above are all designed for transferring drops of an aqueous liquid. However, all the above-described constructions can be adapted for use with any other kind of liquid such as organic liquids by appropriately selecting materials which have the corresponding relative affinities for the particular liquid to be transferred.

What is claimed is:

1. A method of transferring drops of liquid on to a substrate comprising dipping a dropping pin into a source of liquid to be transferred, removing the dropping pin from the source of liquid, and transferring drops of liquid from the dropping pin to one or more substrates, wherein a surface of the dropping pin for contact with the liquid has a first region comprising a capillary channel leading to a reservoir located within the dropping pin and exhibiting an affinity to the liquid to be transferred, and a second region located about the entrance to the capillary channel and exhibiting a lower affinity to the liquid to be transferred than the first region, the relative affinities of the first and second regions for the liquid to be transferred being selected such that when the dropping tool is dipped into and then removed from a source of the liquid to be transferred, the liquid adheres to the first region without substantially any adherence of the liquid to the second region.

2. The method according to claim 1 wherein the capillary channel is formed by a technique selected from the group consisting of electron discharge machining, laser ablation and focussed ion beam etching.

3. The method according to claim 1 wherein the entrance to the capillary channel is located at the tip of the pin.

4. The method according to claim 1 wherein the dropping pin has a tip and at least one surface tapered towards the tip, and wherein the entrance to the capillary channel is located at a position on the tapered surface remote from the tip.

5. The method according to claim 1 wherein the boundary between the first and second regions is topologically discontinuous.

6. The method according to claim 1 wherein the liquid to be transferred is an aqueous liquid, the first region is relatively hydrophilic and the second region is relatively hydrophobic.

7. The method according to claim 1 wherein the first region is comprised of a first material having an affinity for the liquid to be transferred and the second region is comprised of a second material having a lower affinity for the liquid to be transferred than the first material.

8. The method according to claim 1 wherein the capillary channel is of a size suitable for carrying a drop of liquid having a diameter of 1 mm or less.

9. A dropping pin for transferring drops of a liquid onto a substrate comprising a surface for contact with the liquid having a first region including a capillary channel leading to a reservoir located within said dropping pin and exhibiting an affinity to the liquid to be transferred, and a second region located about an entrance to the capillary channel and exhibiting a lower affinity to the liquid to be transferred than the first region, the relative affinities of the first and second regions for the liquid to be transferred being selected such that when the dropping pin is dipped into and then removed from a source of the liquid to be transferred, the liquid adheres to the first region without substantially any adherence of the liquid to the second region, said capillary channel and reservoir formed by removing selected portions of a pin substrate.

10. The dropping pin according to claim 9 wherein the first region is relatively hydrophilic and the second region is relatively hydrophobic.

11. The dropping pin according to claim 9, wherein the entrance to the capillary channel is located at the tip of the pin.

12. The dropping pin according to claim 9 comprising a tip and at least one surface tapered towards the tip, and wherein the entrance to the capillary channel is located at a position on the tapered surface remote from the tip.

13. The dropping pin according to claim 9 wherein the capillary channel is of a size suitable for carrying a drop of liquid having a diameter of about 1 mm or less.

14. The dropping pin according to claim 4 wherein the capillary channel is formed by a technique selected from the group consisting of electron discharge machining, laser ablation and focussed ion beam etching.

15. A dropping tool for transferring drops of liquid on to a substrate, comprising a surface for contact with the liquid which includes a first region which exhibits an affinity to the liquid to be transferred directly surrounded by a second region which exhibits a lower affinity to the liquid to be transferred than the first region, the boundary between the first and second regions being topologically discontinuous, and the relative affinities of the first and second regions for the liquid to be transferred being selected such that when the dropping tool is dipped into and then removed from a source of the liquid to be transferred, the liquid adheres to the first region without substantially any adherence of the liquid to the second region.

16. A dropping tool for transferring drops of a liquid onto a substrate and having a surface for contact with the liquid, said surface comprising a first region including a capillary channel leading to a reservoir located within the dropping tool and exhibiting an affinity to the liquid to be transferred, and a second region located about an entrance to the capillary channel and exhibiting a lower affinity to the liquid to be transferred than the first region, the capillary channel having the entrance located at a position remote from a tip of the dropping tool and on a portion of said surface tapered toward the tip, and the relative affinities of the first and second regions for the liquid to be transferred being selected such that when the dropping tool is dipped into and removed from a source of the liquid to be transferred, the liquid adheres to the first region without substantially any adherence of the liquid to the second region.

17. A method of transferring drops of liquid onto a substrate comprising dipping a dropping tool into a source of liquid to be transferred, removing the dropping tool from the source of liquid, and transferring drops of liquid from the dropping tool onto one or more substrates, a surface of the dropping tool having a first region which exhibits an affinity to the liquid to be transferred directly surrounded by a second region which exhibits a lower affinity to the liquid to be transferred than the first region, the boundary between the first and second regions being topologically discontinuous, and the relative affinities of the first and second regions for the liquid to be transferred being selected such that when the dropping tool is dipped into and then removed from a source of liquid to be transferred, the liquid adheres to the first region without substantially any adherence of the liquid to the second region.

* * * * *